United States Patent [19]

Brindöpke et al.

[11] Patent Number: 4,892,954

[45] Date of Patent: Jan. 9, 1990

[54] PROCESS FOR THE PREPARATION OF 2-OXO-1,3-DIOXOLANES

[75] Inventors: Gerhard Brindöpke, Frankfurt am Main; Manfred Marten, Mainz, both of Fed. Rep. of Germany

[73] Assignee: Hoechst AG, Fed. Rep. of Germany

[21] Appl. No.: 111,979

[22] Filed: Oct. 21, 1987

Related U.S. Application Data

[63] Continuation-in-part of Ser. No. 894,334, Aug. 8, 1986, abandoned.

[30] Foreign Application Priority Data

Aug. 16, 1985 [DE] Fed. Rep. of Germany ....... 3529263

[51] Int. Cl.$^4$ ............................................. C07D 317/12
[52] U.S. Cl. ..................................... 549/229; 549/230
[58] Field of Search ................................ 549/229, 230

[56] References Cited

U.S. PATENT DOCUMENTS 3,535,342 10/1970 Emmons ............................. 549/229

FOREIGN PATENT DOCUMENTS 31682 7/1980 Japan .

Primary Examiner—Glennon H. Hollrah
Assistant Examiner—Amelia A. Owens
Attorney, Agent, or Firm—Bierman and Muserlian

[57] ABSTRACT

Process for the preparation of 2-oxo-1,3-dioxolanes by reaction of epoxides with carbon dioxide in the presence of a catalyst, wherein at least one epoxy compound is mixed with at least one catalyst in the presence or absence of an inert solvent and is reacted at temperatures from 40° to 180° C. while introducing carbon dioxide at normal pressure or slightly increased pressure to form the corresponding organic carbonates. The 2-oxo-1,3-dioxolanes obtained are used to prepare synthetic resins containing urethane groups in the form of coatings and molded bodies.

9 Claims, No Drawings

PROCESS FOR THE PREPARATION OF 2-OXO-1,3-DIOXOLANES

This is a continuation-in-part application of application Ser. No. 894,336 filed on Aug. 8, 1986 by Brindöpke et al, now abandoned.

It is known that 2-oxo-1,3-dioxolanes (also termed alkylene carbonates) can be obtained by reacting alkylene oxides with carbon dioxide in the presence of catalysts. In German Offenlegungsschrift No. 2,611,087 a process is described for the preparation of alkylene carbonates of the general formula

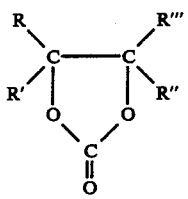

an alkylene oxide being reacted with $CO_2$ at temperatures between 0° and 200° C. and a pressure of 1 to 98 bar in the presence of a catalyst which consists of a combination of a protic substance of the formula ROH and a nitrogen-containing base. Protic substances are water, alcohols and phenol. Trimethylamine, triethylamine, pyridine or dimethylaniline are quoted as nitrogen-containing bases. With respect to the substituents R to R''' it is only stated generally that these may be hydrogen or an alkyl, aryl, cycloalkyl or aralkyl radical. More detailed information is not given. In the examples only ethylene oxide and propylene oxide are quoted as alkylene oxides and all the work is carried out under pressure (10 bar minimum).

In "Monatshefe für 115 (1984), 205–214, G Rokicki and co-workers describe the preparation of cyclic carbonates from $CO_2$ and oxiranes int he presence of alkali-metal salt/phase transfer catalysts. Crown ethers, 1,4-diazabicyclo[2,2,2]-octane (DABCO), N,N,N,N-tetramethylethylene diamine (TMEDA) and triethylbenzylammonium chloride (TEBA) and also (with reduced yield) polyethylene glycol are used as phase transfer agents. High yields, i.e. almost theoretical values, are achieved only by means of initial pressures of 40 bar. If 6 bar is employed, a yield which is lower by approximately 25% is obtained, and for 1 bar a yield of even only 8% is obtained. Ethylene oxide and propylene oxide, epihalohydrines, glycidol, n-butyl, allyl and phenyl glycidol ethers, styrene oxide and 3,3-disubstituted cyclohexene oxide are quoted as epoxy components.

A further paper by G. Rokicki (Makromol. Chem. 186, 331–337 (1985)) described the preparation of cyclic dicarbonates by the use of 2,2-bis[4-(2,3-epoxypropoxy)phenyl]propane or an epoxy resin ((R) Epikote 828) under the conditions specified above.

The preparation of alkylene carbonates by treatment of alkylene oxides with $CO_2$ in the presence of an alcohol such as methanol and an (un)substituted phosphine compound as catalyst is additionally known (PCT WO 84/03, 701). Increased pressure (21 bar) is also employed in this case. In addition, it emerges from the publication that the presence of both the alcohol and also of the phosphine is absolutely essential to obtain a good yield.

It therefore emerges from the prior art that to achieve a high yield high pressures must always be employed, that a catalyst mixture which contains a cocatalyst must be used, and/or that the presence of a protic substance is necessary to achieve satisfactory yields.

The disadvantages mentioned can be avoided according to the present invention.

The subject of the invention is therefore a process for the preparation of 2-oxo-1,3-dioxolanes by reaction of epoxides with carbon dioxide in the presence of a catalyst, wherein at least epoxy compound is mixed with at least one catalyst in the presence or absence of an inert solvent and is reacted at temperatures from 40° to 180° C. while introducing carbon dioxide at normal pressure or slightly increased pressure to form the corresponding organic carbonates. The epoxy groups in the starting compounds can be partially or completely reacted by this process.

The advantage of the process is the application of normal or slightly increased pressure, no large equipment expenditure being necessary. Furthermore, the high selectivity of the reaction should be emphasized, i.e. virtually no epoxy side-reactions such as homopolymerization occur which have been described for this reaction mechanism in the state of the art. Furthermore, it is possible to produce storage-stable epoxy/carbonate mixtures by the process which have a multifunctionality and are available for many fields of application.

The pressure to be used in the process is in general 1 to 10, preferably 1 to 5 and in particular 1 to 3 bar. In most cases normal pressure is used, but if necessary increased pressure can also be employed. The preferred temperature range of the process is 50 to 160, in particular 60° to 145° C. The following compounds are, for example, suitable as epoxy components which can be reacted with $CO_2$ and which in general have at least one terminal epoxy group: aliphatic epoxides containing at least 6 carbon atoms such as hexene, octene, and dodecene 1-oxides, glycidol and epihalohydrines of the formula

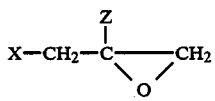

in which Z represents a hydrogen atom, a methyl or ethyl group and X represents a halogen atom or an OH group. Examples of such epihalohydrines are epichlorohydrine, epibromohydrine, 1,2-epoxy-2-methyl-3-chloropropane and 1,2-epoxy-2-ethyl-3-chloropropane.

Further epoxy components which may be used according to the invention include, for example, epoxy components which contain on average at least one terminal 1,2-epoxy group. Preferably these are epoxy compounds which contain on average at least one substituted or unsubstituted glycidyl ether group or a substituted or unsubstituted glycidyl ester group, furthermore, epoxidized, multiply unsaturated compounds and epoxides containing amide or urrethane groups.

Epoxy compounds which contain on average at least one substituted or unsubstituted glycidyl ether group which has the formula

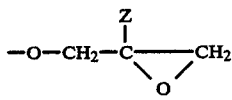

(3)

in which Z represents hydrogen, a methyl or an ethyl group, are, for example, glycidyl or polyglycidyl ethers of phenol or polyhydric phenols which have one or more aromatic nuclei and also of novolacs, polyglycidyl ethers of alcoholic polyhydroxyl compounds obtained by an addition reaction of polyhydric phenols containing one or more aromatic nuclei with alkylene oxides which have 2 to 4 carbon atoms, and polyglycidyl ethers of alcoholic polyhydroxyl compounds which have one or more alicyclic rings. Phenol, the various cresols, resorcin, hydroquinone, pyrogallol, phloroglucine, 1,5-, 2,7-, 2,6-dihydroxynaphthalenes and the like, 2,2-bis(p-hydroxyphenyl)propane and 2,2-bis(p-hydroxyphenyl)methane (known as bisphenol A or F respectively, 2,4'-dihydroxydiphenylmethane and the like are, for example, used as phenols. Polyhydric alcohols which can be reacted to form glycidyl ethers are, for example, ethylene glycol, propylene glycol, butyl glycol, neopentyl glycol, hexylene glycol, polyethylene glycol, polypropylene glycol and the like.

Among these are included also plasticized epoxy resins with terminal epoxy groups which are prepared by partial reaction of the epoxy groups of epoxy resins containing at least two epoxy groups with substances containing OH and COOH such as polyhydric alcohols, for example, the abovementioned diols, polycarboxylic acids or polyesters containing carboxyl or OH groups.

Further epoxy compounds are glycidyl esters of saturated or ethylenically unsaturated carboxylic acids containing at least one substituted or unsubstituted glycidyl ester group of the following formula

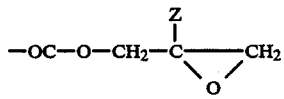

(4)

in which Z represents a hydrogen atom, a methyl or an ethyl group. The acids are aliphatic or aromatic, saturated or unsaturated mono or polycarboxylic acids, for example acrylic acid, methacrylic acid, adipic acid, the various phthalic acids, tetrahydro- and hexahydro phthalic acid and the like. A very common glycidyl ester is available commercially and is the glycidyl ester of a mixture of saturated monocarboxylic acids with a chain length of 9 to 11 carbon atoms consisting mainly (approximately 94%) of tertiary acids (glycidyl ester of Versatic acid). Included here are also epoxy resins which have been obtained by copolymerization of glycidyl methacrylate with other copolymerizable monomers such as styrene and (meth)acrylic acid esters. Furthermore, epoxides containing amide or urethane groups are suitable for the reaction, for example triglycidyl isocyanurate or glycidol-masked hexamethylene diisocyanate. Mixtures of the epoxy compounds mentioned may also be used.

Compounds which affect the reaction of the epoxides with $CO_2$ catalytically are quaternary ammonium compounds of the formula $(R^1, R^2, R^3, R^4)N^{\oplus}X^{\ominus}$ (6)

in which $R^1$, $R^2$, $R^3$ and $R^4$ are identical or different and may be alkyl groups containing 1 to 4 carbon atoms in the alkyl group or benzyl. X denotes chlorine, bromine, iodine, OH and $CO_3$. Examples of these compounds are triethylammonium bromide, triethylammonium iodide, choline, benzyltrimethylammonium hydroxide, benzyltrimethylammonium carbonate, benzyltributylammonium chloride, 3-chloro-2-hydroxypropyltrimethylammonium chloride, tetraethylammonium hydroxide and bromide and the like. Further catalysts are phosphanes (formerly termed phosphines) of the formula $(R^5, R^6, R^7)$ P, in which $R^5$, $R^6$ and $R^7$ are identical or different and represent aryl or aralkyl groups containing 6 to 12 carbon atoms, for example triphenylphosphane, tritolylphosphane, ditolylphenylphosphane, trianisylphosphane and tribenzylphosphane. Further catalysts are amines such as 1,4-diazabicyclo[2.2.2]octane (DABCO), dimethylaminoethanol, piperazine, 4-dimethylaminopyridine (DMAP), 4-(1-pyrrolidinyl-pyridine), etc., guanidines, for example N,N,N'-tetramethylguanidine and amidines such as 1,5-diazabicyclo[4.3.0]non-5-ene (DBN), 1,8-diazabicyclo[5.4.0]undec-7-ene (DBU) etc., and also imidazole, alkyl-substitution products thereof in the 1, 2, 4 and 5 position containing up to 4 carbon atoms in the alkyl radical such as 1-methylimidazole, 2-methylimidazole, 2-ethyl-4-methylimidazole etc., aryl- and aralkyl-substituted imidazoles such as 2-phenylimidazole, 2-phenyl-4-methylimidazole etc.

The catalysts are in general used alone or mixed in quantities of 0.02 to 10, preferably 0.05 to 6 and in particular 0.05 to 3 percent by weight referred to the weight of the epoxy component.

The reaction time may vary within wide limits. In general the reaction is carried out in a manner such that the epoxy groups are virtually completely reacted. The reaction is followed, for example, by titration of the epoxy groups and is terminated at the point which, within the framework of analytical accuracy, is regarded as "low in epoxy groups or epoxy-free". In this manner alkyl carbonates are obtained from any epoxy compounds which can be processed further in a known manner.

In addition, if polyepoxides are present, the reaction can be terminated at any desired point so that compounds are obtained which, in addition to carbonate groups, also have epoxy groups which are still intact. The latter has the advantage that, depending on the nature of the desired further processing and the application of the products, a selective reaction of the epoxy group in the presence of the carbonate group (and vice versa) can take place. In general, in the case of polyepoxides (number of epoxy groups $n \geq 2$) the reaction will be carried out in this case in a manner such that the proportion of reacted epoxy groups is 0.1–0.9 n.

The action of the catalysts can be improved by adding, as cocatalysts, halides or carbonates of alkali metals or alkaline earth metals in quantities of 0.1 to 10, preferably 0.2 to 5 and in particular 0.4 to 2.5% by weight, referred to the epoxy component, to the mixtures. In this case the chlorides, bromides, iodides or carbonates of the metals lithium, sodium, potassium, magnesium and calcium may be used, KI and NaI being preferred. However, the cocatalysts are in general only used if an increase in reactivity is desired and if, in addition, they do not impair the usability and can be removed by simple operations.

The reaction of the epoxy compounds with $CO_2$ may take place in the presence or absence of solvents. In general no solvents are used if the epoxy compounds exist in the liquid state above 50° C. However, if they are viscous melts at the reaction temperature and as a result make a homogeneous dispersion of the carbon dioxide difficult on stirring or if a further processing of the reaction product in solution is envisaged, solvents are in general used.

Aromatic hydrocarbons such as toluene, xylene and hydrocarbon mixtures produced in petroleum cracking, and furthermore ethers such as dioxane, tetrahydrofuran, glycol and diglycol dimethylether, and other solvents which are inert towards epoxy groups can be used as solvents.

In the following examples P always denotes parts by weight and % always denotes % by weight.

EXAMPLES

General specification for the preparation of biscarbonates from diglycidyl ethers of bisphenol A Examples 1 to 38

A technical diglycidyl ether of bisphenol A with the epoxide content quoted in the Table, if appropriate, dissolved in the specified solvent, was introduced into an apparatus (if appropriate, pressurized apparatus) equipped with stirrer, thermometer and a gas inlet tube and heated to the specified reaction temperature after adding the catalyst, and if appropriate, the co-catalyst while stirring and while introducing carbon dioxide. When employing pressure, the reaction apparatus was flushed out beforehand with carbon dioxide. "®Beckopox EP 140" (epoxide content 8.6%) and "Beckopox EP 301" (epoxide content 3.3%) manufactured by Hoechst AG were used as glycidyl ethers.

Stirring was continued while continuously introducing carbon dioxide at the stated reaction temperatures and pressures until the desired residual epoxide content was reached which was determined by titration. If insoluble catalysts were used filtration was then carried out while hot and the solvent present was, if appropriate, distilled off under reduced pressure.

In Example 1–7 the preparation of epoxy resins containing carbonate groups obtained by partial reaction of diglycidyl ethers of bisphenol A is described. Examples 37 and 38 are comparison experiments according to the prior art.

The biscarbonates prepared according to the Examples 8 to 36 can be recrystallized from methoxypropanol; the product of Example 16, for example, had the following properties after recrystallization:

IR absorption: 1790 cm

Elementary analysis: $C_{found}$: 64.4 $C_{cal}$, 64.5, $H_{found}$: 5.8 $H_{cal}$, 5.6.

Carbonate content as bound $CO_2$: 18.6%.

Abbreviations used in Table 1:

BTBA: Benzyltributylammonium chloride
BTMA: Benzyltrimethylammonium chloride
Choline: N-(2-hydroxyethyl)trimethylammonium hydroxide (45% in methanol)
CHPTMA: 3-chloro-2-hydroxypropyltrimethylammonium chloride
DABCO: 1,4-diazabicyclo[2.2.2]octane
DBN: Diazabicyclo[4.3.0]-nonene-(5)
DGDME: Diglycol dimethyl ether
DMAP: 4-dimethylaminopyridine
TEBA(sic): Tetraethylammonium bromide
TMG: 1,1,3,3-tetramethylguanidine
TPP: Triphenylphosphane
Triton B: Benzyltrimethylammonium hydroxide (40% in methanol)
TTP: tritolylphosphane

TABLE 1

| Example | Diglycidylether Epoxide Content (%) | Diglycidylether Quantity (Parts) | Catalyst | Quantity (Parts) | % | Cocatalyst | Quantity (Parts) | % |
|---|---|---|---|---|---|---|---|---|
| 1 | 8.6 | 30000 | TPP | 380 | 1.3 | — | — | — |
| 2 | 8.6 | 30000 | Triton B | 270 | 0.9 | — | — | — |
| 3 | 8.6 | 1000 | " | 5 | 0.5 | — | — | — |
| 4 | 8.6 | 1000 | TPP | 2 | 1.2 | KI | 9 | 0.9 |
| 5 | 3.3 | 1000 | Triton B | 5 | 0.5 | — | — | — |
| 6 | 8.6 | 1716 | DABCO | 4 | 0.23 | — | — | — |
| 7 | 8.6 | 1488 | TTP | 9.8 | 0.66 | — | — | — |
| 8 | 8.6 | 186 | BTBA | 2.5 | 1.34 | KI | 2 | 1.1 |
| 9 | 8.6 | 186 | BTMA | 1.8 | 1.0 | KI | 2 | 1.1 |
| 10 | 8.6 | 186 | CHPTMA | 1.9 | 1.0 | $K_2CO_3$ | 2 | 1.1 |
| 11 | 8.6 | 186 | TPP | 2.5 | 1.34 | NaI | 1.1 | 0.6 |
| 12 | 8.6 | 186 | " | 2.6 | 1.4 | LiI | 2.3 | 1.23 |
| 13 | 8.6 | 186 | " | 2.6 | 1.4 | $CaCl_2$ | 1.5 | 0.8 |
| 14 | 8.6 | 186 | DABCO | 1.0 | 0.5 | KI | 2.0 | 1.1 |
| 15 | 8.6 | 186 | TPP | 3 | 1.6 | NaBr | 2.0 | 1.1 |
| 16 | 8.6 | 186 | " | 2.6 | 1.4 | KI | 1.1 | 0.6 |
| 17 | 8.6 | 186 | Triton B | 4.5 | 2.4 | KCl | 1 | 0.5 |
| 18 | 8.6 | 30000 | TPP | 400 | 1.3 | KCl | 210 | 0.7 |
| 19 | 8.6 | 1860 | TEBA | 21 | 1.12 | KI | 20 | 1.1 |
| 20 | 8.6 | 1860 | TTP | 27 | 1.45 | NaI | 10 | 0.55 |
| 21 | 8.6 | 30000 | Triton B | 270 | 0.9 | — | — | — |
| 22 | 8.6 | 1618 | Choline | 9.4 | 0.6 | — | — | — |
| 23 | 8.6 | 1000 | TPP | 7 | 0.7 | NaI | 4 | 0.4 |
| 24 | 8.6 | 1000 | Triton B | 9 | 0.9 | — | — | — |
| 25 | 8.6 | 1000 | " | 9 | 0.9 | — | — | — |
| 26 | 3.3 | 1286 | " | 4.5 | 0.35 | — | — | — |
| 27 | 3.3 | 1221 | " | 4 | 0.33 | — | — | — |
| 28 | 8.6 | 1412 | DBN | 3.76 | 0.27 | — | — | — |
| 29 | 8.6 | 1407 | TMG | 3.5 | 0.25 | — | — | — |
| 30 | 8.6 | 1110 | TMG | 2.8 | 0.25 | — | — | — |
| 31 | 8.6 | 1180 | DMAP | 3.1 | 0.26 | — | — | — |
| 32 | 8.6 | 1370 | 2-ethyl-4-methyl- | 3.2 | 0.23 | — | — | — |

TABLE 1-continued

| | | | | imidazole | | | | |
|---|---|---|---|---|---|---|---|---|
| 33 | 8.6 | | 1277 | 2-ethyl-4-methyl-imidazole | 3.0 | 0.23 | — | — |
| 34 | 8.6 | | 1338 | 1-methylimidazole | 2.9 | 0.2 | — | — |
| 35 | 8.6 | | 1185 | 2-methylimidazole | 2.1 | 0.2 | — | — |
| 36 | 8.6 | | 1225 | Imidazole | 1.8 | 0.15 | — | — |
| 37 (V1) | 8.6 | | 1315 | Triethylamine | 9 | 0.7 | — | — |
| 38 (V2) | 8.6 | | 1286 | Triethylamine | 39 | 3.0 | — | — |

| Example | Solvent | Quantity (Parts) | Temp. (°C.) | Pressure (bar) | Reaction time (h) | Yield % | Yield (Parts) | Melting point ($F_p$) | Epoxide content (%) | Bound $CO_2$ content (%) |
|---|---|---|---|---|---|---|---|---|---|---|
| 1 | — | — | 130 | 2 | 16 | | 33700 | — | 3.8 | 10.2 |
| 2 | — | — | 120 | 2 | 5 | | 33200 | — | 4.0 | 9.8 |
| 3 | DGDME | 200 | 120 | 1 | 4 | | 1090 | — | 4.5 | 8.5 |
| 4 | xylene | 200 | 120 | 1 | 7 | | 1080 | — | 4.2 | 9.4 |
| 5 | — | 300 | 120 | 1 | 8 | | 1039 | — | 1.5 | 4.3 |
| 6 | — | — | 120 | 1 | 16 | | 1908 | — | 2.7 | 12.5 |
| 7 | n-butanol | 372 | 118 | 1 | 12 | — | 1585 | — | 3.5 | 11.1 |
| 8 | — | — | 140 | 1 | 16 | 97.1 | 222 | 50–53 | 0.2 | 18.6 |
| 9 | — | — | 120 | 1 | 20 | 97.8 | 223 | 49–52 | 0.3 | 18.4 |
| 10 | — | — | 120 | 1 | 12 | 97.2 | 223 | 51–53 | 0.1 | 18.6 |
| 11 | — | — | 120 | 1 | 17 | 97.9 | 224 | 52–53 | 0.2 | 18.5 |
| 12 | — | — | 120 | 1 | 19 | 96.2 | 220 | 51–52 | 0.2 | 18.5 |
| 13 | — | — | 140 | 1 | 29 | 96.5 | 219 | 48–50 | 0.5 | 18.0 |
| 14 | — | — | 120 | 1 | 14 | 97.8 | 223 | 51–52 | 0.3 | 18.5 |
| 15 | — | — | 130 | 1 | 24 | 96.9 | 221 | 50–52 | 0.3 | 18.1 |
| 16 | — | — | 120 | 1 | 18 | 97.9 | 224 | 50–52 | 0.2 | 18.6 |
| 17 | — | — | 130 | 1 | 13 | 96.5 | 220 | 51–53 | 0.3 | 18.0 |
| 18 | — | — | 130 | 2 | 26 | 95.5 | 35790 | 49–51 | 0.4 | 18.2 |
| 19 | — | — | 140 | 2 | 17 | 98.5 | 2260 | 51–53 | 0.1 | 18.7 |
| 20 | — | — | 130 | 1 | 27 | 95.8 | 2180 | 51–53 | 0.4 | 18.1 |
| 21 | — | — | 120 | 2 | 17 | 97.5 | 36050 | 51–53 | 0.1 | 18.0 |
| 22 | — | — | 120 | 1 | 19 | 92.3 | 1826 | 49–52 | 0.4 | 17.7 |
| 23 | DGDME | 300 | 120 | 1 | 12 | 97.8 | 1205 | 50–51 | 0.2 | 18.4 |
| 24 | DGDME | 200 | 120 | 1 | 15 | 96.9 | 1195 | 46–47 | 0.1 | 18.1 |
| 25 | xylene | 200 | 120 | 1 | 16 | 97.6 | 1200 | 47–50 | 0.2 | 17.9 |
| 26 | xylene | 322 | 130 | .1 | 24 | 92.9 | 1296 | — | 0.2 | 7.8 |
| 27 | DGDME | 398 | 130 | 1 | 20 | 95.0 | 1265 | — | 0.05 | 7.6 |
| 28 | — | — | 120 | 1 | 16 | 96.8 | 1685 | 51–52 | 0.1 | 18.1 |
| 29 | DGDME | 352 | 120 | 1 | 11 | 95.3 | 1654 | 53–57 | 0.1 | 18.3 |
| 30 | DGDME | 10 | 100 | 1 | 19 | 95.4 | 1295 | 56–57 | 0.4 | 18.0 |
| 31 | DGDME | 10 | 100 | 1 | 15 | 92.8 | 1350 | 125–138 | 0.1 | 18.7 |
| 32 | DGDME | 15 | 100 | 1 | 15 | 92.0 | 1550 | 112–131 | 0.2 | 18.4 |
| 33 | — | — | 100 | 1 | 16 | 91.2 | 1420 | 49–52 | 0.5 | 17.8 |
| 34 | DGDME | 10 | 100 | 1 | 18 | 90.2 | 1480 | 51–53 | 0.3 | 18.2 |
| 35 | — | 10 | 100 | 1 | 17 | 91.8 | 1320 | 49–51 | 0.7 | 17.3 |
| 36 | — | — | 120 | 1 | 17 | 95.5 | 1438 | 53–55 | 0.2 | 18.3 |
| 37 (V1) | n-butanol | 329 | 120 | 1 | 16 | | | — | 0.5 | — |
| 38 (V2) | n-butanol | 322 | 120 | 1 | | Gelation after 1 h | | | | |

39

254 P of a diglycidyl ether of a commercial polypropylene glycol described as "epoxy resin DER 736" manufactured by Dow, USA (epoxide content: 8.3%) were heated with 2.2 P of potassium iodide and 3.5 P of benzyltributylammonium chloride at 120° C. while at the same time passing carbon dioxide through for 20 hours. At the end of the reaction time the reaction mixture was filtered and cooled. Yield: 280 P (90.5%) of a viscous bright yellow resin. IR absorption: 1804 cm$^{-1}$, epoxide content: 0.3%, bound $CO_2$ content: 17.1%.

40

326 P of diglycidyl ether of a commercial polypropylene glycol described as "epoxy resin DER 732" manufactured by Dow, USA (epoxide content: 4.9%) were mixed with 1 P of potassium chloride and, while simultaneously introducing carbon dioxide, with 1.6 P of, and a 40% solution of, benzyltrimethylammonium hydroxide in methanol. Stirring was then continued at 120° C. while introducing carbon dioxide until the epoxide content was <0.2%. 339 P (91.9%) of a viscous clear resin is obtained. IR absorption: 1804 cm$^{-1}$, epoxide content: 0.11%, bound $CO_2$ content: 11.1%.

41

142 P of glycidyl methacrylate, 1.3 P of triphenylphosphane and 0.6 P of potassium iodide were heated at 80° C. in the presence of 0.3 P of the monomethyl ether of hydroquinone.

The stirring was continued for 17 hours while passing carbon dioxide through. After filtering and cooling 181 P (98.1%) of a clear yellow viscous liquid were obtained.

Epoxide content: 0.3%,
Elementary analysis: $C_{found}$: 51.3%, $C_{cal}$: 51.6%, $H_{found}$: 5.6%, $H_{cal}$: 5.4%.
Boiling point: 135°–137° C./0.1–0.2 Torr.

42

142 P of glycidyl methacrylate, 0.7 P of diazabicyclooctane and 0.5 P of lithium iodide were heated at 80° C. in the presence of 0.3 P of the monomethylether of hydroquinone.

Stirring was continued for 9 hours while passing $CO_2$ through and, after filtering and cooling, 179 P (96.8%)

of a clear yellow liquid were obtained. Epoxide content: 0.2%, boiling point: 136° C./0.1–0.2 Torr.

43

1420 P of glycidyl methacrylate, 13 P of triphenylphosphane and 5 P of sodium iodide were stirred at 80° C. in a pressurized apparatus for 10 hours in the presence of 3 P of the monomethylether of hydroquinone with a constant carbon dioxide pressure of 1.5 bar. After filtration, 1780 P (95.5%) of a bright yellow viscous liquid were obtained. IR absorption: 1797, 1723 cm$^{-1}$, epoxide content: 0.3%.

44

260 P of a glycidyl ester of Versatic acid (epoxy content: 6.2%) were mixed with 2 P of a 40% solution of benzyltrimethylammonium hydroxide in methanol and 0.5 P of potassium chloride at room temperature while passing carbon dioxide through. While introducing further carbon dioxide, the mixture was then heated at 120° C. and stirring was continued for 12 hours until an epoxide content of 0.3% was reached. Yield: 300 P (99%) of a bright yellow viscous liquid. IR absorption: 1733, 1801 cm$^{-1}$, epoxide content: 0.25%, bound $CO_2$ content: 14.1%.

45

260 P of a glycidyl ester of Versatic acid (epoxide content: 6.2%), 4.7 P of triphenylphosphane and 3.3 P of potassium iodide were heated at 120° C. for 18 hours while passing carbon dioxide through. Yield: 299 P (98.9%) of a bright yellow viscous liquid. IR absorption: 1733, 1801 cm$^{-1}$, epoxide content: 0.25%, bound $CO_2$ content: 14.1%.

46

128 P of octene 1-oxide, 2.2 P of triphenylphosphane and 1.9 P of potassium iodide were heated at 120° C. while passing carbon dioxide through and stirring was continued until the epoxide content was <0.2%. After filtration, 125 P (93.3%) of a clear yellow liquid were obtained. IR absorption: 1800 cm$^{-1}$, epoxy content: 0.1%, bound $CO_2$ content: 22.9%.

47

565 P of dodecene 1-oxide, 5.7 P of tetraethylammonium-bromide and 1.9 P of sodium iodide were heated at 120° C. while passing carbon dioxide through and stirring was continued until the epoxide content was 21 0.5%. After filtration, 674 P (97.1%) of a clear yellow liquid were obtained. IR absorption: 1800 cm$^{-1}$, epoxide content: 0.3%, bound $CO_2$ content 18.7%.

48

300 P of a technical 1,3-neopentylglycol diglycidyl ether (epoxide content: 10.7%) were mixed at room temperature with 1.3 P of triton B while introducing carbon dioxide and heated at 120° C. While continuously introducing carbon dioxide, stirring was continued until the epoxide content was <0.3% (approx. 17 hours). 351 P (94.7%) of a bright yellow liquid is obtained. IR absorption: 1794 cm$^{-1}$, epoxide content: 0.1%, bound $CO_2$ content: 21.9%.

49

282 P of a technical butane-1,4-diol diglycidyl ether (epoxide content: 11.4%) were reacted with carbon dioxide at 120° C. in the presence of 1.3 P of Triton B as in Example 48. 341 P (92.8%) of a viscous liquid were obtained. IR absorption: 1793 cm$^{-1}$, epoxide content: 0.25%, bound $CO_2$ content: 22.6%.

50

320 P of a technical hexane-1,6-diol diglycidyl ether (epoxide content 1) were reacted with carbon dioxide in the presence of 1.3 P of Triton B as in Example 48. 379 P (93.2%) of a bright yellow resin are obtained. IR absorption: 1794 cm$^{-1}$, epoxide content: <0.1, bound $CO_2$ content: 20.4%.

51

330 P of a commercial novolak containing glycidyl ether groups (DEN 731 manufactured by DOW Chemicals) (epoxide content: 9.1%) were dissolved in 141 P of diglycol dimethyl ether and mixed with 1.2 P of 4-dimethylaminopyridine while simultaneously passing carbon dioxide through. After heating to 100° C. stirring was continued while continuously introducing carbon dioxide until the epoxide content was <0.1% (duration approx. 16 hours). After distilling off the solvent under reduced pressure 380 P (92.4%) of a clear colorless novolak containing carbonate groups were obtained. Epoxide content: 0.1%, bound $CO_2$ content: 19.0%.

52

200 P of commercial glycidyl ether ("Beckopox EP 080" manufactured by Hoechst AG) (epoxide content: 8%) were mixed with 0.5 P of 2-ethyl-4-methylimidazole at 25° C. and heated at 110° C. while passing carbon dioxide through. Stirring was then continued until the epoxide content was <0.3%. Yield: 218 (90.1%) of a bright yellow viscous liquid. Epoxide content: 0.3%, bound $CO_2$ content: 17.1%.

53

260 P of a commercial triglycidyl isocyanurate ("®Araldite PT 810" manufactured by Ciba-Geigy) were mixed with 260 P of diglycol dimethyl ether and 1 P of 2-ethyl-4-methylimidazole and heated at 120° C. while introducing carbon dioxide. While introducing further carbon dioxide, stirring was continued until the epoxide content was <0.5%, whereupon a white crystalline product precipitated. After completion of the reaction, the precipitate was filtered off with suction and dried at 60° C. Yield: 318 P (86.7%) of a white crystalline compound. Melting point: 204°–210° C. (decomposition), epoxide content: 0.9%, bound $CO_2$ content: 27.4%.

54

300 P of polyethylene adipate (prepared from 10 ml of ethylene glycol and 11 mol of adipic acid by azeotropic esterification, OH number: 56) were dissolved in 90 P of diethylene glycol dimethyl ether and heated at 70° C. After adding 0.1 P of 4-dimethylamino pyridine, 44 P of phthalic anhydride were added in small amounts. After reaching an acid number of 40 the reaction mixture was mixed with 118 P of technical diglycidyl ether of bisphenol A type (Beckopox EP 140, epoxide content 8.6%) and with 0.3 P of chromium (III) octoate, and heated at 110° C. After an acid number of 1 had been reached, the mixture was heated at 120° C. after adding 0.5 P of 4-dimethylaminopyridine and while introducing carbon dioxide, and stirring was continued until the epoxide content was <0.05%. Yield:

550 P of a clear, viscous resin solution, epoxide content: 0.04%, bound $CO_2$ content: 2.0%.

55

The reaction products of Examples 24 and 37 (comparison 1) were investigated for their composition by gel permeation chromatography. The carrier material of the column was a polystyrene made by Waters Millipore described as Ultrastyragel (1000–100 Å, 1000 psi).

| Example | % content of biscarbonate | Monocarbonate | Bisepoxide | Polymer proportion |
|---|---|---|---|---|
| 24 | 90.2 | 7.0 | — | 2.8 |
| 37 (VI) | 27.9 | 5.9 | — | 66.2 |

The investigation clearly shows the selectivity of the reaction of epoxy compounds with $CO_2$ according to the invention. While the polymer proportion remains virtually unchanged compared with that of the technical epoxide used under these circumstances, the polymer content rises to 66.2%, referred to the total mass, on using triethylamine as a catalyst.

If the triethylamine addition is increased, for example to 3% as in Example 38 (comparison 2), the mixture gels after a reaction time of one hour.

We claim:

1. A process for the preparation of 2-oxo-1,3-dioxolanes by reaction of epoxides with carbon dioxide in the presence of a catalyst, wherein at least one epoxy compound is mixed with at least one catalyst of the group consisting of 4-dimethyl aminopyridine, 4-(1-pyrrolidinyl)-pyridine, amidines, imidazoles, and is reacted in the presence or absence of an inert solvent at temperatures from 40° to 180° C. while introducing carbon dioxide at normal pressure or slightly increased pressure up to 10 bar to form the corresponding organic carbonates.

2. Process as claimed in claim 1, wherein a pressure of 1 to 10 bar is employed.

3. Process as claimed in claim 1, wherein the catalyst is used in quantities of 0.02 to 10% by weight, referred to the epoxy component.

4. Process as claimed in claim 1, wherein the reaction of the epoxy compound with carbon dioxide is only partially carried out.

5. Process as claimed in claim 1, wherein imidazole, 1-methyl-imidazole, 2-methylimidazole and 2-ethyl-4-methylimidazole are used as catalysts.

6. Process as claimed in claim 1, wherein the epoxy compounds have at least one terminal 1,2-epoxy-group.

7. Process as claimed in claim 1, wherein aliphatic epoxides with at least 6 carbon atoms or epoxides of the formula (2)

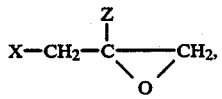

in which Z is a hydrogen atom, a methyl or ethyl group and X is a halogen atom or an OH group, are used as the epoxy compounds.

8. Process as claimed in claim 1, wherein those compounds which contain on average at least one substituted or unsubstituted glycidyl ether group of the formula (3)

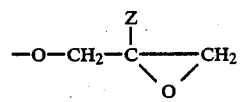

or a substituted or unsubstituted glycidyl ester group of the formula (4)

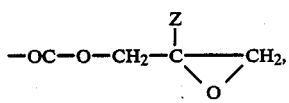

Z having the meaning already mentioned in both formulae, and furthermore epoxidized, multiply unsaturated compounds and epoxides containing amide and urethane groups are reacted as epoxy compounds.

9. Process as claimed in claim 1, wherein polyglycidyl ether, plasticized epoxy resins with terminal epoxy groups, glycidyl esters of saturated or ethylenically unsaturated (poly)carboxylic acids are reacted.

* * * * *